United States Patent [19]
Benazzi et al.

[11] Patent Number: 5,773,678
[45] Date of Patent: Jun. 30, 1998

[54] USE OF AN OMEGA ZEOLITE BASED CATALYST COMPRISING AT LEAST ONE METAL FROM GROUPS IIA, IVB, IIB OR IVA FOR THE DISMUTATION AND/OR TRANSALKYLATION OF ALKYLAROMATIC HYDROCARBONS

[75] Inventors: Eric Benazzi, Montesson; Fabio Alario, Neuilly sur Seine, both of France

[73] Assignee: Institut Francais du Petrole, France

[21] Appl. No.: 796,188

[22] Filed: Feb. 7, 1997

[30] Foreign Application Priority Data

Feb. 9, 1996 [FR] France .................................. 96 01605

[51] Int. Cl.$^6$ ....................................................... C07C 5/00
[52] U.S. Cl. .......................... 585/470; 585/474; 585/475; 585/467
[58] Field of Search .................................. 585/470, 474, 585/475, 467

[56] References Cited

U.S. PATENT DOCUMENTS 5,210,356  5/1993  Shamshoum et al. .................. 585/475
5,391,528  2/1995  Benazzi et al. .......................... 502/66

FOREIGN PATENT DOCUMENTS 2 291 957   6/1976   France .
2 303 782  10/1976   France .
25 58 035   6/1977   Germany .

*Primary Examiner*—Elizabeth D. Wood
*Attorney, Agent, or Firm*—Millen, White, Zelano & Branigan, P.C.

[57] ABSTRACT

The invention concerns the use of a catalyst comprising at least one zeolite having a mazzite type structure in its acid form, the catalytic properties of the catalyst having been modified by depositing, on the external surface of the crystals, at least one metal selected from metals from group IIa of the periodic classification of the elements, such as Be, Mg, Ca, Sr or Ba, group IVb, such as Ti, Zr or Hf, group IIb such as Zn, Cd or Hg and group IVa such as Ge, Sn or Pb, said catalyst also comprising at least one matrix and, optionally at least one element selected from the group formed by IB and VIII of the periodic classification of the elements, for the dismutation of alkylaromatic hydrocarbons, preferably for the dismutation of toluene to produce benzene and xylenes, and/or for the transalkylation of alkylaromatic hydrocarbons, preferably for the transalkylation of toluene and trimethylbenzenes to produce xylenes.

12 Claims, No Drawings

5,773,678

USE OF AN OMEGA ZEOLITE BASED CATALYST COMPRISING AT LEAST ONE METAL FROM GROUPS IIA, IVB, IIB OR IVA FOR THE DISMUTATION AND/OR TRANSALKYLATION OF ALKYLAROMATIC HYDROCARBONS

FIELD OF THE INVENTION

The invention concerns the use of a catalyst comprising at least one zeolite with structure type mazzite in its acid form, the catalytic properties of the catalyst having been modified by depositing, on the external surface of the crystals, at least one metal selected from metals from group IIa of the periodic classification of the elements, such as Be, Mg, Ca, Sr or Ba, group IVb, such as Ti, Zr or Hf, group IIb such as Zn, Cd or Hg and group IVa such as Ge, Sn or Pb, said catalyst also comprising at least one matrix and, optionally at least one element selected from the group formed by groups IB and VIII of the periodic classification of the elements, for the dismutation of alkylaromatic hydrocarbons, preferably for the dismutation of toluene to produce benzene and xylenes, and/or for the transalkylation of alkylaromatic hydrocarbons, preferably for the transalkylation of toluene and trimethylbenzenes to produce xylenes.

BACKGROUND OF THE INVENTION

The catalyst used in accordance with the invention has been partially described in our European patent application EP-A-0 569 268 and in U.S. Pat. No. 5,391,528. That catalyst comprises at least one omega zeolite in its acid form, with structure type mazzite, with a pore diameter of about 7.4 Å and with a monodimensional microporous network ("Atlas of Zeolite Structure Types", W. M. Meier and D. H. Olson, $3^{rd}$ edition, 1992). The omega zeolite in the catalyst composition has a global Si/Al atomic ratio which is in the range 3.2 to 100, preferably in the range 6 to 80 and more preferably in the range 8 to 60. The sodium content in that zeolite is generally less than 0.6% by weight, preferably less than 0.1% by weight. The catalyst also comprises a matrix and, optionally at least one element selected from the group formed by groups IB and VIII of the periodic classification of the elements. The catalyst described in those documents is used for the isomerisation of a C8 aromatic cut.

SUMMARY OF THE INVENTION

Surprisingly, by means of depositing at least one metal selected from metals from group IIa, IVb, IIb and IVa, in particular Ge, Zr and/or Sn, on the external surface of zeolite crystals with structure type mazzite, preferably omega zeolite, it is possible to obtain catalysts which are active and selective for the dismutation of alkylaromatic hydrocarbons or for the transalkylation of alkylaromatic hydrocarbons.

The present invention thus concerns the use of a catalyst comprising at least one zeolite with structure type mazzite, preferably an omega zeolite, at least partially, preferably practically completely in its acid form, the catalyst comprising, on the external surface of its crystals, at least one metal selected from metals from group IIa, IVb, IIb and IVa of the periodic classification of the elements, said catalyst also comprising at least one matrix and, optionally at least one element selected from the group formed by groups IB and VIII of the periodic classification of the elements, for the dismutation and/or for the transalkylation of alkylaromatic hydrocarbons.

The dismutation and/or transalkylation of alkylaromatic hydrocarbons is generally carried out under the following conditions: a temperature which is in the range 250° C. to 600° C., preferably in the range 330° C. to 500° C.; a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

The catalyst used in accordance with the invention, based on a zeolite with structure type mazzite, preferably based on an omega zeolite, has improved catalytic performances, in particular improved selectivity, with respect to prior art catalysts based on omega zeolite.

In particular, the catalyst used in accordance with the present invention is very effective for the dismutation of toluene and/or transalkylation of toluene and C9+ alkylaromatic hydrocarbons (i.e., containing at least 9 carbon atoms per molecule), in particular toluene and trimethylbenzenes. This results in a large reduction in undesirable secondary reactions such as the formation of polyalkylaromatic compounds containing at least 9 carbon atoms per molecule.

The catalyst used in accordance with the present invention has already been described in our European patent application EP-A-0 569 268, and in U.S. Pat. No. 5,391,528, for the particular case (which is preferred in the present invention) where the zeolite with structure type mazzite is omega zeolite. However, as an indication, its characteristics will be summarised below. The catalyst generally contains 10% to 99%, preferably 20% to 95%, of zeolite with structure type mazzite. When the catalyst contains at least one element selected from the group formed by groups IB and VIII of the periodic classification of the elements, said element(s) is (are) generally present in an amount which is in the range 0.01% to 10% by weight, preferably in the range 0.05% to 7% by weight, and more preferably in the range 0.10% to 5% by weight. The complement to 100% generally consists of the matrix in the catalyst.

The matrix comprised in the catalyst of the present invention is generally selected from members of the group formed by clays (for example from natural clays such as kaolin or bentonite), magnesia, aluminas, silicas, titanium oxide, boron oxide, zirconia, aluminium phosphates, titanium phosphates, zirconium phosphates and silica-aluminas, preferably from members of the group formed by aluminas and clays.

The zeolite with structure type mazzite comprised in the catalyst used in accordance with the invention is generally selected from the group formed by omega zeolite, mazzite, LZ-202 zeolite, gallosilicate mazzite zeolite or ZSM-4 zeolite, preferably omega zeolite, with a principal pore diameter of about 7.4 Å and with a monodimensional microporous network ("Atlas of Zeolite Structure Types", W. M. Meier and D. H. Olson, $3^{rd}$ edition, 1992).

The zeolite with structure type mazzite, comprising silicon and at least one element T selected from the group formed by gallium and aluminium, preferably aluminium, has a global Si/T atomic ratio in the range 3.2 to 100, preferably in the range 6 to 80, and more preferably in the range 8 to 60, and a sodium content of less than 0.6% by weight with respect to the dry zeolite weight, preferably less than 0.1% by weight.

When, as is preferred, T is aluminium, an unrefined synthesised zeolite with structure type mazzite is dealuminized using any method which is known to the skilled person, in particular the method described in U.S. Pat. No. 4,780,436 when T is aluminium, i.e., a calcining step carried out in a stream of dry air, to eliminate the organic structuring agent occluded in the microporosity of the zeolite, followed by at least one ion exchange step using at least one $NH_4NO_3$ solution, to eliminate practically all alkaline cations, in particular sodium, present in a cationic position in the zeolite, then at least one framework dealuminization cycle comprising at least one calcining step in the presence of steam at a temperature which is generally in the range 550° C. to 850° C., followed by at least one acid attack step.

In the preferred case when T is Al, the framework dealuminization cycle, comprising at least one calcining step carried out in steam and at least one attack step in an acid medium, can be repeated as many times as is necessary to obtain the dealuminized zeolite with structure type mazzite with the desired characteristics. Similarly, following calcining in steam, a number of successive acid attack steps using different concentrations of acid solutions can be carried out.

Deposition of at least one metal selected from the group formed by metals from groups IIa, IVb, IIb and IVa on the external surface of the crystals of said zeolite is generally carried out by grafting using at least one organometallic compound of the metal as the grafting agent, which compound is generally sufficiently bulky not to penetrate into the interior of the microporous network of the omega zeolite and can react with the OH groups on the surface. In the case of tin, the grafting agents can be compounds with formula $SnR^1R^2R^3R^4$ where groups $R^1$, $R^2$, $R^3$, $R^4$, which may be identical or different, are organic groups of varying bulk, in general of large bulk; non limiting examples are alkyl, aryl, organosilyl vinyl, polynuclear aryl, cycloalkyl, allyl, propargyl radicals. Groups $R^i$, where i=1,2,3 or 4, can also be a bulky alkoxy or aryloxy type group, for example a terbutoxy, o,o'-diphenylphenoxy, o,o'-diisopropylphenoxy group, etc. . . . Group $R^i$ can also be a hydride, but at least one organic $R^i$ group remains fixed on the tin, such as in compounds $SnBu_2H_{2\ or\ SnBu3}H$.

In the general case of metals from group IIa (Be, Mg, Ca, Sr, Ba, Ra) and metals from groups IVb (Ti, Zr, Hf), IIb (Zn, Cd, Hg) and IVa (Ge, Sn, Pb), other than tin, the grafting agents can also be compounds with formula $BeR_2$, $MgR_2$, $CaR_2$, $SrR_2$, $BaR_2$, $RaR_2$, $TiR_4$, $ZrR_4$, $HfR_4$, $CdR_4$, $HgR_2$, $GeR_4$, $SnR_4$ or $PbR_4$, where $R^i$, which may be identical or different, are organic groups such as those defined above.

For tin, a preferred grafting agent is tetrabutyl tin, $SnB_4$. For magnesium, a preferred grafting agent is bis-neopentylmagnesium $MgNp_2$. For zirconium, a preferred grafting agent is tetra-neopentylzirconium $ZrNp_4$. For germanium, a preferred grafting agent is tetrabutylgermanium $GeBu_4$.

Preparation of the grafted zeolite comprises a first pretreatment step for the zeolite with structure type mazzite, generally using one of the following two methods: activation in an inert stream, such as nitrogen, or vacuum pretreatment. A second step is grafting the zeolite with structure type mazzite. Thus at least one grafting agent is fixed on the zeolite in the gas phase or in the liquid phase. In the latter case, the selected organometallic compound is placed in solution in a solvent, for example hexane, in an inert gas. A third step consists of decomposing the organic fragments, generally by decomposition in an oxidising atmosphere or by vacuum decomposition.

The optional deposit of at least one other metal selected from metals from groups IIa, IVb, IIb or IVa is carried out in analogous fashion using the methods described above.

At the end of the thermal decomposition step, the amount of metal (metals) selected from groups IIa, IVb, IIb and/or IVa is in the range 0.01% to 5%, advantageously in the range 0.01% to 4%, of the zeolite with structure type mazzite.

Nevertheless, the degree of selectivity of the zeolite with structure type mazzite can optionally be regulated by, if necessary, carrying out a supplemental "metal grafting—calcining" cycle using one of the techniques described above, to reach a metal (metals) content of more than 5%, or even 7%, on the zeolite with structure type mazzite.

The acidic properties of the zeolite with structure type mazzite are not altered by deposition of the metal (metals) using the techniques described above. Thus the zeolite with structure type mazzite obtained has a sodium content of less than 2000 ppm by weight with respect to the weight of dry zeolite with structure type mazzite, a global Si/T atomic ratio which is in the range 5 to 100, preferably in the range 6 to 80, and more preferably in the range 8 to 60.

The characteristics of the zeolite with structure type mazzite can be measured by the following techniques:
in the preferred case when T is aluminium, the Si/Al atomic ratio is determined by X ray fluorescence and by silicon 29 nuclear magnetic resonance;
the sodium content is determined by atomic absorption;
the elementary cell volume and crystallinity are determined by X ray diffraction, the omega zeolite sample being prepared as described in the method in standard ASTM D3942 80 set up for faujasite.

The catalyst can be prepared using any method which is known to the skilled person. In general, it is obtained by mixing the matrix and the zeolite then forming. The optional element from the group formed by groups IB and VIII of the periodic classification of the elements can be introduced either before forming, or during mixing, or to the zeolite itself before mixing it, or, as is preferable, after forming. Forming is generally followed by calcining, generally at a temperature which is in the range 250° C. to 600° C. The optional element from the group formed by groups IB and VIII of the periodic classification of the elements can be introduced after the calcining step. In all cases, the element is generally chosen to be deposited either, as is preferable, practically completely on the zeolite, or practically completely on the matrix, or partially on the zeolite and partially on the matrix, the choice being effected, in a manner which is known to the skilled person, by means of the parameters used during said deposition, such as the nature of the precursor selected to effect said deposition.

The element from groups IB or VIII, preferably selected from the group formed by Ag, Ni and Pt, and more preferably Ni, can also be deposited on the zeolite-matrix mixture which has been pre-formed using any procedure which is known to the skilled person. Such deposition is generally carried out by the techniques of dry impregnation, ion exchange(s) or co-precipitation. When ion exchange is carried out using precursors based on silver, nickel or platinum, the salts which are generally used are silver salts such as chlorides or nitrates, a tetramine complex of platinum, or nickel salts such as chlorides, nitrates, acetates or formates. The ion exchange technique can also be used to deposit the metal directly on the zeolite powder before optional mixing with a matrix.

When the catalyst contains a plurality of metals, these latter can be introduced either in the same way or using different techniques, before or after forming and in any order. When the technique used is ion exchange, a plurality of successive exchanges may be necessary to introduce the required quantities of metals.

As an example, one preferred method for preparing the catalyst of the invention consists of mixing the zeolite in a wet matrix gel (generally obtained by mixing at least one acid and a matrix powder), for example alumina, for the time required to obtain good homogeneity of the paste thus produced, i.e., for about ten minutes, for example, then passing the paste through a die to form extrudates with a diameter which is, for example, in the range 0.4 to 4 mm. After oven drying for several minutes at 100° C. and after calcining, for example for 2 hours at 400° C., the optional element, for example nickel, can be deposited, for example by ion exchange, said deposit being followed by final calcining, for example for 2 hours at 400° C.

The catalyst of the invention is generally formed so that the catalyst is preferably in the form of pellets, aggregates, extrudates or spherules, depending on its use.

Catalyst preparation is generally finished by calcining, termed final calcining, normally at a temperature which is in the range 250° C. to 600° C., preferably preceded by drying, for example oven drying, at a temperature which is generally in the range from ambient temperature to 250° C., preferably in the range 40° C. to 200° C. The drying step is preferably carried out during the period of temperature rise required to carry out the calcining step.

The invention concerns the use of the catalyst for the dismutation of alkylaromatic hydrocarbons, preferably for the dismutation of toluene to produce benzene and xylenes, and/or for the transalkylation of alkylaromatic hydrocarbons, preferably for the transalkylation of generally $C_9^+$ alkylaromatic hydrocarbons (i.e., containing at least 9 carbon atoms per molecule), such as transalkylation and/or dismutation of toluene and/or $C_9^+$ alkylaromatics to produce xylenes. The feed for such a process can comprise 0 to 100% of $C_9^+$ alkylaromatics and 0 to 100% of toluene.

The operating conditions are generally as follows: a temperature which is in the range 250° C. to 600° C., preferably in the range 330° C. to 500° C.; a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

The following examples illustrate the invention without in any way limiting its scope.

EXAMPLE 1

Preparation of Zeolites 1 and 2, in Accordance With the Invention

The starting material used was an omega zeolite with a global Si/Al atomic ratio of 3.2, a sodium content of about 5.3% with respect to the weight of dry omega zeolite, an elementary cell volume of 2.196 nm$^3$ and a pore volume in nitrogen of 0.125 cm$^3$ liquid per gram, measured at −196° C. and at $P/P_0=0.19$.

This omega zeolite was initially "dry" calcined at 550° C. in a stream of air and nitrogen for 6 hours. The solid obtained was then subjected to three ion exchange steps in a 10N NH$_4$NO$_3$ solution at about 100° C. for 4 hours for each exchange step. The omega zeolite then underwent hydrothermal treatment in the presence of 50% of steam at 600° C. for 4 hours. The zeolite underwent acid attack with 1N nitric acid at about 100° C. for 2 hours, to extract the extra-network aluminium species formed during hydrothermal treatment. The volume V of the nitric acid used (in ml) was 10 times the weight W of the dry omega zeolite (V/W=10). The omega zeolite thus treated then underwent another hydrothermal treatment step, in the presence of 50% of steam but this time at 700° C. for 4 hours, then acid attack using a 1.5N nitric acid solution at about 100° C. for 4 hours, to extract the extra-network aluminium species formed during hydrothermal treatment. The volume V of the nitric acid used (in ml) was 10 times the weight W of the dry omega zeolite (V/W=10).

After these treatments, the omega zeolite in its H form had a global Si/Al atomic ratio of 25, a sodium content of 90 ppm by weight with respect to the weight of dry omega zeolite, an elementary cell volume of 2.115 nm$^3$ and a nitrogen adsorption capacity of 0.206 cm$^3$ of liquid N$_2$/g, measured at −196° C. and at $P/P_0=0.19$.

Tin was then grafted onto the external surface of the crystals of omega zeolite in its H form using the liquid phase method described above. The organic fragments bonded to the tin after the grafting step could be decomposed under vacuum or in the presence of air (oxidising atmosphere).

i) Liquid phase grafting and decomposition of organic fragments under vacuum.

The following successive steps were carried out:

Activation of the omega zeolite by treatment in an inert gas at 150° C. for 12 hours then reduction of the temperature to 20° C., in an inert gas.

Calcining any possible traces of organic compounds adsorbed on the zeolite in a stream of dry air (0.4 l/h/g) and an inert gas (2 l/h/g) for 2 hours at 550° C. then solely in a stream of dry air (2 l/h/g) for 2 hours, still at 550° C.

Cooling the omega zeolite to 20° C. in an inert gas and suspension in hexane. Tetrabutyl tin was then injected, still in an inert gas atmosphere.

After stirring for 15 minutes, the solvent was eliminated under vacuum. The temperature of the omega zeolite was then raised to 150° C., then kept at this temperature for 6 hours in an inert atmosphere. After cooling the zeolite to ambient temperature, the excess SnBu$_4$ was eliminated by rinsing with a fresh hexane solution.

The organic butyl fragments bonded to the tin were then decomposed by heat treatment under vacuum. To this end, the omega zeolite was placed under dynamic vacuum for 2 hours at 450° C. then in a stream of inert gas for 2 hours.

The solid obtained after these treatments was referred to as Ω1: its tin content was 1.3% by weight. Its other characteristics remained unchanged compared to those of the omega zeolite in its H form.

ii) Liquid phase grafting and decomposition of organic fragments in an oxidising atmosphere The omega zeolite was produced and grafted in identical fashion to that described above in respect of the preparation of solid Ω1. The only change was the decompositoin of the organic butyl fragments bonded to the tin which was carried out in an oxidising atmosphere in the presence of a mixture of oxygen and an inert gas at 450° C. for 4 hours.

The solid obtained was referred to as Ω2: the tin content was 1.26%. The other characteristics were the same as those for the omega zeolite in its H form.

EXAMPLE 2

Preparation of Catalysts C3 and C4, in Accordance With the Invention

The Ω1 grafted zeolite from Example 1 was formed by extrusion with an alumina gel to obtain catalyst C3 after drying and calcining in dry air. Catalyst C3 contained 80% by weight of grafted omega zeolite and 20% by weight of alumina.

Similarly, the Ω2 zeolite from Example 1 was formed by extrusion with an alumina gel to obtain catalyst C4 after drying and calcining in dry air. Catalyst C4 contained 80% by weight of grafted omega zeolite and 20% by weight of alumina.

EXAMPLE 3

Preparation of Catalyst C5, in Accordance With the Invention

In this example, catalyst C4 from Example 2 underwent three ion exchange steps with a nickel acetate solution to introduce 1% by weight of nickel into the catalyst.

To this end, catalyst C4 was brought into contact with a 0.5M solution of $Ni(CH_3CO_2)_2$ at ambient temperature, with stirring. Between each exchange, the solid was separated from the impregnating solution and washed with abundant quantities of deionised water. The concentration of impregnating solution was readjusted to 0.5 moles per liter for each exchange.

The wet solid was dried at 120° C. for 12 hours and calcined in a stream of dry air at 500° C. for one hour. Catalyst C5 obtained contained 79.32% by weight of grafted omega zeolite in its hydrogen form, 19.83% by weight of alumina and 0.85% by weight of nickel.

EXAMPLE 5

Preparation of Catalyst C6, in Accordance With the Invention

The omega zeolite used to prepare catalyst C6 was the dealuminised zeolite in its hydrogen form prepared in Example 1 with the following characteristics: a global Si/Al atomic ratio of 25, a sodium content of 90 ppm by weight with respect to the weight of dry omega zeolite, an elementary cell volume of 2.115 $nm^3$ and a nitrogen adsorption capacity of 0.206 $cm^3$ of liquid $N_2$/g, measured at -196° C. and at $P/P_0$=0.19.

Germanium was deposited on the external surface of the omega zeolite crystals using the gas phase method. The following successive steps were carried out:

Activation of the zeolite under dynamic vacuum at 160° C. for 8 hours. The temperature was then increased at a rate of 2° C./min to 450° C. and kept at that temperature for 9 hours under dynamic vacuum. The temperature was reduced to 250° C., at which temperature $GeBu_4$ was injected. The omega zeolite was left under the vapour tension of the $GeBu_4$ for 48 hours at 250° C. After cooling to ambient temperature (20° C.), the released gases were eliminated under dynamic vacuum then the physisorbed residual species were desorbed under dynamic vacuum for 8 hours at 220° C. The butyl fragments fixed on the germanium were then decomposed by heat treatment in an oxidising atmosphere. This treatment was carried out in the presence of a mixture of oxygen and an inert gas, at 450° C. for 4 hours.

The solid obtained after these treatments was referred to as Ω6: it contained 0.31% by weight of germanium. Its other characteristics remained unchanged, remaining those of the H form of the omega zeolite.

The grafted omega zeolite Ω6 obtained above was then formed by extrusion with an alumina gel to obtain an extruded solid containing 80% by weight of omega zeolite and 20% of alumina after drying and calcining in dry air.

The extrudates obtained were brought into contact with a 0.5M solution of $Ni(CH_3CO_2)_2$ at ambient temperature, with stirring. Between each exchange, the solid was separated from the impregnating solution and washed with abundant quantities of deionised water. The concentration of impregnating solution was readjusted to 0.5 moles per liter for each exchange.

The wet solid was dried at 120° C. for 12 hours and calcined in a stream of dry air at 500° C. for one hour. Catalyst C6 obtained contained 79.32% by weight of omega zeolite in its hydrogen form, 19.83% by weight of alumina and 0.85% by weight of nickel.

EXAMPLE 6

Preparation of Catalyst C7, Not in Accordance With the Invention

The starting material used was the same omega zeolite in its H form as that prepared in Example 1. It had a global Si/Al atomic ratio of 25, a sodium content of 90 ppm with respect to the weight of dry omega zeolite, an elementary cell volume of 2.115 $nm^3$ and a nitrogen adsorption capacity of 0.206 $cm^3$ liquid $N_2$/g, measured at -196° C. and at $P/P_0$=0.19.

This zeolite did not undergo grafting using at least one element selected from metals from groups IIa, IVb, IIb and IVa.

The non-grafted omega zeolite was then formed by extrusion with an alumina gel to obtain an extruded solid containing 80% by weight of omega zeolite and 20% of alumina after drying and calcining in dry air.

The extrudates obtained were brought into contact with a 0.5M solution of $Ni(CH_3CO_2)_2$ at ambient temperature, with stirring. Between each exchange, the solid was separated from the impregnating solution and washed with abundant quantities of deionised water. The concentration of impregnating solution was readjusted to 0.5 moles per liter for each exchange.

The wet solid was dried at 120° C. for 12 hours and calcined in a stream of dry air at 500° C. for one hour. Catalyst C7 obtained contained 79.32% by weight of omega zeolite in its hydrogen form, free of extra-network aluminium species, 19.83% by weight of alumina and 0.85% by weight of nickel.

The following table provides a synopsis of catalysts C3, C4, C5, C6 and C7 (in % by weight):

| Catalysts | Sn or Ge content with respect to zeolite | Nickel, with respect to catalyst | Alumina | Amount of grafted zeolite in catalyst |
|---|---|---|---|---|
| C3 | 1.3 (Sn) | 0 | 20 | 80 |
| C4 | 1.26 (Sn) | 0 | 20 | 80 |
| C5 | 1.26 (Sn) | 0.85 | 19.83 | 79.32 |
| C6 | 0.31 (Ge) | 0.85 | 19.83 | 79.32 |
| C7 | 0 | 0.85 | 19.83 | 79.32 |

EXAMPLE 7

Evaluation of Catalyst Performances

The catalysts were used in a fixed bed reactor under pressure, into which the feed, constituted by pure toluene, was introduced.

The table below compares the yields of (benzene+ ethylbenzene+xylenes) obtained using catalysts C5 and C6, in accordance with the invention, and C7, not in accordance with the invention:

| Catalyst | C5 (invention) | C6 (invention) | C7 (not invention) |
|---|---|---|---|
| Reaction temperature (°C.) | 430 | 430 | 430 |
| Total reaction pressure (bar) | 40 | 40 | 40 |
| Yields, % by weight (benzene + ethylbenzene + xylenes) | 37.8 | 37.6 | 36.9 |

Comparison of catalysts C5 and C6 with catalyst C7 shows that the catalysts of the invention, C5 and C6, lead to (benzene+ethylbenzene+xylenes) yields which are greater than those obtained with non-conforming catalyst C7.

We claim:

1. A process for the production of xylene from a feed consisting essentially of at least one of toluene and an alkylaromatic compound having at least 9 carbon atoms per molecule, said process comprising subjecting said feed to dismutation and/or transalkylation reactions, said production being conducted in the presence of a catalyst comprising at least one zeolite having a mazzite structure, the catalyst comprising, on the external surface of crystals of said zeolite, at least one metal selected from the group consisting of metals from groups IIa, IVb, IIb and IVa of the periodic classification of the elements, said catalyst also comprising at least one matrix and, optionally at least one element selected from the group consisting of groups IB and VIII of the periodic classification of the elements.

2. A process according to claim 1, in which said zeolite is selected from the group consisting of gallosilicate mazzite zeolite, mazzite, LZ-202 zeolite, omega zeolite, and ZSM-4 zeolite.

3. A process according to claim 1, in which said zeolite is omega zeolite.

4. A process according to claim 1, in which said catalyst contains 10% to 99% of zeolite with structure type mazzite and, optionally, when the catalyst contains at least one element selected from the group consisting of groups IB and VIII of the periodic classification of the elements, said element(s) are present in an amount which is in the range 0.01% to 10% by weight, the complement to 100% by weight consisting of the matrix of the catalyst.

5. A process according to claim 1, in which the matrix is selected from members of the group consisting of clays, magnesia, aluminas, silicas, titanium oxide, boron oxide, zirconia, aluminium phosphates, titanium phosphates, zirconium phosphates and silica-aluminas.

6. A process according to claim 1, in which deposition of at least one metal selected from the group consisting of metals from groups IIa, IVb, IIb and IVa is carried out by grafting using at least one organometallic compound of said metal as a grafting agent.

7. A process according to claim 1, carried out under the following conditions: a temperature which is in the range 250° C. to 600° C.; a pressure which is in the range 10 to 60 bar; a supply space velocity, expressed in kilograms of feed introduced per kilogram of catalyst per hour, in the range 0.1 to 10; and a hydrogen to hydrocarbons molar ratio which is in the range 2 to 20.

8. A process according to claim 1 comprising the dismutation of toluene to form benzene and xylenes.

9. A process according to claim 1 comprising the transalkylation of toluene with an alkyl aromatic having 9 carbon atoms per molecule to produce xylenes.

10. A process according to claim 9 further comprising the dismutation of toluene to form benzene and xylene.

11. A process according to claim 1, wherein the process produces a higher percentage of xylene than the same process using said at least one zeolite devoid of said at least one metal on the external surface of said crystals.

12. A process according to claim 11, wherein said metal is tin or germanium.

* * * * *